US011426449B2

(12) United States Patent
Heslet

(10) Patent No.: US 11,426,449 B2
(45) Date of Patent: *Aug. 30, 2022

(54) METHODS AND COMPOSITIONS FOR ENHANCING PULMONARY HOST DEFENSE IN ACUTE AND CHRONIC RADIATION SYNDROME, THERAPEUTIC RADIATION INTERVENTION AND CANCER THERAPY

(71) Applicant: REPONEX PHARMACEUTICALS A/S, Hoersholm (DK)

(72) Inventor: Lars Heslet

(73) Assignee: REPONEX PHARMACEUTICALS A/S, Hoersholm (DK)

( * ) Notice: Subject to any disclaimer, the term of this patent is extended or adjusted under 35 U.S.C. 154(b) by 350 days.

This patent is subject to a terminal disclaimer.

(21) Appl. No.: 15/822,820

(22) Filed: Nov. 27, 2017

(65) Prior Publication Data

US 2018/0078614 A1 Mar. 22, 2018

Related U.S. Application Data

(62) Division of application No. 14/009,855, filed as application No. PCT/DK2012/050114 on Apr. 10, 2012, now Pat. No. 9,855,316.

(60) Provisional application No. 61/472,864, filed on Apr. 7, 2011.

(51) Int. Cl.
*A61K 38/19* (2006.01)
*C07K 14/535* (2006.01)
*A61K 9/00* (2006.01)

(52) U.S. Cl.
CPC .......... *A61K 38/193* (2013.01); *C07K 14/535* (2013.01); *A61K 9/0073* (2013.01)

(58) Field of Classification Search
CPC .............. A61K 2300/00; A61K 38/193; A61K 9/0073; A61P 43/00; A61P 37/04; C07K 14/535
See application file for complete search history.

(56) References Cited

U.S. PATENT DOCUMENTS

| 9,855,316 B2 | 1/2018 | Heslet | ................ | A61K 37/193 |
| 2008/0299071 A1* | 12/2008 | Pettit | ................ | A61K 9/0019 |
| | | | | 424/85.1 |

FOREIGN PATENT DOCUMENTS

| WO | WO 2008/052567 A2 | 5/2008 |
| WO | WO 2008/109818 A1 | 9/2008 |
| WO | WO 2012/136224 A2 | 10/2012 |
| WO | WO 2012/136224 A3 | 10/2012 |

OTHER PUBLICATIONS

Allen, J.C. et al. High-dose cyclophosphamide chemotherapy for recurrent CNS tumors in children. J. Neurology, 1981, 55:749-756.*
Balzarotti, M., et al. Activity of single agent vinorelbine in pre-treated non-Hodgkin's lymphoma. Annals of Oncology, 1996, 7:970-972.*
Blum, K.A., et al. Prolonged myelosuppression with clofarabine in the treatment of patients with relapsed or refractory, aggressive non-Hodgkin lymphoma. Leukemia and Lymphoma, 2009, 50(3):349-356.*
Gwak, H-H., et al. ACNU-cisplatin continuous infusion chemotherapy as salvage therapy for recurrent glioblastomas: phase II study. J. Neuro-Oncology, 2005, 75:173-180.*
Quezada, G., et al. Intranasal granulocyte-macrophage colony-stimulating factor reduces the Aspergillus burden in an immunosuppressed murine model of pulmonary aspergillosis. Antimicrobial Agents and Chemotherapy, 2008, 52(2):716-718.*
Butturini et al. "Use of Recombinant Granulocyte-Macrophage Colony Stimulating Factor in the Brazil Radiation Accident" The Lancet 1988 332:471-475.
Donnelly et al. "Acute Radiation Syndrome: Assessment and Management" Southern Medical Journal 2010 103(6) :541-544.
Edmonson et al. "Granulocyte-Macrophage Colony-Stimulating Factor. Preliminary Observations on the Influences of Dose, Schedule, and Route of Administration in Patients Receiving Cyclophosphamide and Carboplatin" Cancer 1992 70(10) :2529-2539 [Abstract Only].
Hérodin, F. and Drouet, M. "Cytokine-Based Treatment of Accidentally Irradiated Victims and New Approaches" Experimental Hematology 2005 33:1071-1080.
Herrmann et al. "Effect of Granulocyte-Macrophage Colony-Stimulating Factor on Neutropenia and Related Morbidity Induced by Myelotoxic Chemotherapy" The American Journal of Medicine 1990 88:619-624.
Heslet et al. "Acute Radiation Syndrome (ARS)—Treatment of the Reduced Host Defense" International Journal of General Medicine 2012 5:105-115.
Kouvaris et al. "Dermatitis During Radiation for Vulvar Carcinoma: Prevention and Treatment with Granulocyte-Macrophage Colony-Stimulating Factor Impregnated Gauze" Wound Repair and Regeneration 2001 9:187-193.
Monroy et al. "Recovery from Severe Hematopoietic Suppression Using Recombinant Human Granulocyte-Macrophage Colony-Stimulating Factor" International Society for Experimental Hematology 1988 16:344-348.
Nidhi et al. "The Optimal Use of Granulocyte Macrophage Colony Stimulating Factor in Radiation Induced Mucositosis in Head and Neck Squamous Cell Carcinoma" Journal of Cancer Research and Therapeutics 2005 1(3) :136-141.
Rao et al. "Aerosolized Granulocyte Macrophage Colony-Stimulating Factor (GM-CSF) Therapy in Metastatic Cancer" American Journal of Clinical Oncology 2003 26(5) :493-498.

(Continued)

*Primary Examiner* — Prema M Mertz
(74) *Attorney, Agent, or Firm* — Licata & Tyrrell P.C.

(57) ABSTRACT

Methods and compositions for treating and alleviating symptoms of irradiation injuries, therapeutic radiation intervention and/or anti-cancer therapies in a subject via pulmonary airway administration of granulocyte macrophage colony stimulating factor (GM-CSF) or a compound with similar affinity to the specific alveolar GM-CSF receptor to enhance pulmonary host defense are provided.

4 Claims, No Drawings

(56) References Cited

OTHER PUBLICATIONS

Rose et al. "The Effect of Aerosolized Recombinant Human Granulocyte Macrophage Colony-Stimulating Factor on Lung Leukocytes in Nonhuman Primates" American Review of Respiratory Disease 1992 145:1279-1286.
Synodjnou et al. "Administration of GM-CSF as Enemas in the Management of Radiation Proctitis" European Journal of Cancer 2001 37:S358 [Abstract Only].
Waddick et al. "Radioprotective Effects of Recombinant G-CSF, Recombinant GM-CSF and their Combination in Lethally Irradiated Mice" Radiation Oncology, Biology, and Physics 1991 21 (suppl 1): 238, abstract 1090 [Abstract Only].
Waselenko et al. "Medical Management of the Acute Radiation Syndrome: Recommendations of the Strategic National Stockpile Radiation Working Group" Annals of Internal Medicine 2004 140(12) :1037-1051.
Zhang et al. "Efficacy of rhGM-CSF on Acute Oral Mucositosis During Nasopharyngeal Carcinoma Radiotherapy" Chinese Journal of Cancer Prevention and Treatment 2009 16(21) :1673-1675 [Abstract Only].
International Search Report from PCT/DK2012/050114, dated Sep. 25, 2012, PCT.
International Preliminary Report on Patentability from PCT/DK2012/050114, dated Oct. 17, 2013, PCT.
Office Communication dated Sep. 8, 2014 in U.S. Appl. No. 14/009,855, filed Oct. 4, 2013.
Office Communication dated Mar. 16, 2015 in U.S. Appl. No. 14/009,855, filed Oct. 4, 2013.
Office Communication dated Feb. 18, 2016 in U.S. Appl. No. 14/009,855, filed Oct. 4, 2013.
Office Communication dated Dec. 7, 2016 in U.S. Appl. No. 14/009,855, filed Oct. 4, 2013.
Office Communication dated Dec. 20, 2017 in U.S. Appl. No. 14/009,855, filed Oct. 4, 2013.

* cited by examiner

METHODS AND COMPOSITIONS FOR ENHANCING PULMONARY HOST DEFENSE IN ACUTE AND CHRONIC RADIATION SYNDROME, THERAPEUTIC RADIATION INTERVENTION AND CANCER THERAPY

This patent application is a divisional of U.S. application Ser. No. 14/009,855, filed Oct. 4, 2013, which is the U.S. National Stage of PCT/DK2012/050114, filed Apr. 10, 2012, which claims the benefit of priority from U.S. Provisional Application Ser. No. 61/472,864, filed Apr. 7, 2011, teachings of each of which are herein incorporated by reference in their entirety.

FIELD OF THE INVENTION

The present invention relates to methods and compositions for enhancing pulmonary host defense via pulmonary airway administration of granulocyte macrophage colony stimulating factor (GM-CSF) or a compound similar thereto with similar affinity to the specific alveolar GM-CSF receptor. Enhancement of the pulmonary host defense through the methods and compositions of the present invention is useful preemptively in acute radiation syndrome (ARS) and chronic radiation syndrome and before, during and after therapeutic radiation intervention and anti-cancer therapies.

BACKGROUND OF THE INVENTION

The lung has its own local host defense mechanism designed to protect this vital organ from exposure to injury, inflammatory conditions and microbiological agents, both from the inhaled route and from blood circulation. This local host defense mechanism is dependent on endogenous expression of granulocyte macrophage colony stimulating factor (GM-CSF) by the alveolar cells in the alveolar and peripheral airways. This local mechanism is isolated from the systemic circulation since GM-CSF does not pass from the airspaces to the circulation and vice versa. Thus, expression of GM-CSF in the lung does not increase circulating monocytes and neutrophils in the circulation and no functional effects are seen in the lung upon systemic administration of GM-CSF. This is due to the fact that the GM-CSF molecule is too big to traverse the transalveolar-capillary passage. Further GM-CSF molecule is a water-soluble molecule. Without endogenous GM-CSF expression, the resting macrophages of the lung are not activated into the highly immune competent dendritic alveolar cells which orchestrate the lung's local defense mechanism.

SUMMARY OF THE INVENTION

The lung's host defense mechanism is reduced significantly in a number of conditions including, but not limited to, acute or chronic irradiation injury to the lung tissue both from the air side and/or from the direct exposure in inadvertent radiation accidents, therapeutic radiation therapy and treatment of cancer involving systemically administered chemotherapeutics.

An aspect of the present invention relates to methods for enhancing the lung's host defense mechanism in a subject via pulmonary airway administration of granulocyte macrophage colony stimulating factor (GM-CSF) or a compound with similar affinity to the specific alveolar GM-CSF receptor. These methods for enhancing pulmonary host defense in a subject are useful preemptively in acute radiation syndrome (ARS) and chronic radiation syndrome, before, during and after therapeutic radiation intervention and in anti-cancer therapies.

Accordingly, another aspect of the present invention relates to methods for treating or alleviating symptoms in a subject secondary to irradiation injuries, therapeutic radiation intervention and/or anti-cancer therapies and/or the negative pulmonary effect of irradiation injuries, therapeutic radiation intervention and/or anti-cancer therapies on the pulmonary host defense mechanism via pulmonary airway administration of GM-CSF or a compound with similar affinity to the specific alveolar GM-CSF receptor.

Another aspect of the present invention relates to compositions for enhancing the lung's host defense mechanism in a subject comprising GM-CSF or a compound with similar affinity to the specific alveolar GM-CSF receptor formulated for pulmonary airway administration. These compositions can be administered preemptively in acute radiation syndrome (ARS) and chronic radiation syndrome, before, during and after therapeutic radiation intervention and in anti-cancer therapies.

Accordingly, another aspect of the present invention relates to compositions comprising GM-CSF or a compound with similar affinity to the specific alveolar GM-CSF receptor formulated for pulmonary airway administration to a subject for treating or alleviating symptoms secondary to irradiation injuries, therapeutic radiation intervention and/or anti-cancer therapies and/or the negative pulmonary effect of irradiation injuries, therapeutic radiation intervention and/or anti-cancer therapies on the pulmonary host defense mechanism.

DETAILED DESCRIPTION OF THE INVENTION

Inhaled recombinant GM-CSF up-regulates the pulmonary host defense mechanism. By binding to the lung's GM-CSF receptors, GM-CSF transforms the resting alveolar macrophages into immune active dendritic cells, an effect which is not achieved by systemically administered recombinant GM-CSF. Ubiquitous endogenously expressed GM-CSF also fails to achieve this effect on the airside of the lungs due to GM-CSF's large size and its water-soluble qualities.

The present invention provides methods and compositions for treating or alleviating symptoms in a subject secondary to irradiation injuries, therapeutic radiation intervention and/or anti-cancer therapies and/or the negative pulmonary effect of irradiation injuries, therapeutic radiation intervention and/or anti-cancer therapies on the pulmonary host defense mechanism by enhancing the pulmonary host defense mechanism in a subject via pulmonary airway administration of an effective amount of granulocyte macrophage GM-CSF or a compound with similar affinity to the specific alveolar GM-CSF receptor to the subject. Enhancement of the pulmonary host defense leading to treatment or alleviation of symptoms in a subject secondary to irradiation injuries, therapeutic radiation intervention and/or anti-cancer therapies and/or the negative pulmonary effect of irradiation injuries, therapeutic radiation intervention and/or anti-cancer therapies on the pulmonary host defense mechanism can be determined, for example, by monitoring local pulmonary host defense parameters such as changes in white cell count and/or cytokine release from tracheal spirate or obtained from bronchoalveolar lavage. Alternatively or in addition, enhancement of the pulmonary host defense leading to treatment or alleviation of symptoms in a subject secondary to irradiation injuries, therapeutic radiation intervention and/or anti-cancer therapies and/or the negative pulmonary effect of irradiation injuries, therapeutic radiation intervention and/or anti-cancer therapies on the pulmonary host defense mechanism can be determined by flow cytometric analysis of cells from the lung such as alveolar macrophages with or without selected and/or specified surface receptors and/or subgroups recruited by, for example, tracheal aspirate and/or from bronchoalveolar lavage fluid. Methods for flow cytometric analysis of cells from the lung are described Garn et al. in Experimental and Toxicologic Pathology 2006 57:S2:21-24.

GM-CSF for use in the present invention is available through various commercial vendors.

In one embodiment, the GM-CSF is recombinant GM-CSF. In this embodiment, the dose of GM-CSF administered via inhalation can range from about 50 µg/dose/day to 500 µg bid/m$^2$ body surface. In one embodiment, the dose of recombinant GM-CSF administered is 300 µg/day.

In another embodiment, a compound with similar affinity to the specific alveolar GM-CSF receptor is administered via inhalation. Examples of such compounds include, but are not limited to, mimetics of GM-CSF, for example peptidomimetics or small organic molecules with similar specific alveolar GM-CSF receptor affinity as compared to GM-CSF, and recombinantly prepared variant proteins similar in amino acid sequence to GM-CSF but which may comprise modifications to, for example, enhance the pharmacological profile of the compound as compared to GM-CSF. By similar in amino acid sequence it is meant that the protein shares at least 50%, more preferably at least 60%, more preferably at least 70%, more preferably at least 80%, more preferably at least 90%, more preferably at least 95%, and most preferably at least 99% sequence identity with GM-CSF. By similar receptor affinity it is meant that the compound exhibits at least about 10%, preferably at least about 30%, more preferably at least about 50%, and most preferably at least about 70%, of the specific alveolar GM-CSF receptor affinity as GM-CSF.

Examples of specific alveolar GM-CSF receptors include but are not limited to, alveolar macrophage type I and II receptors. Without being bound to any specific theory, it is believed that, like endogenously expressed local pulmonary GM-CSF, inhaled recombinant GM-CSF and compounds with similar affinity to specific alveolar GM-CSF receptors, attach to the specific receptors, thereby transforming the resting alveolar macrophage into an immunoactive dendritic cell. The dendritic cells then orchestrate the immune response by a chain of processes including phagocytosis of microbiological agents, particles and dead cells, with subsequent digestion after which the intracellular lysozomatically digested protein fragments are placed on the dendritic cell surface in order to present these fragments as antigens to recruit systemic immunoactive cells such as T-lymphocytes (CD4+, CD8+, CD16+ & CD20+) neutrophils, which in turn ensure the normal function of pulmonary host defense. By "effective amount" of GM-CSF or a compound similar thereto with similar affinity to the specific alveolar GM-CSF receptor, it is meant a dose, which, when administered to a subject via pulmonary administration, achieves a concentration of GM-CSF or a compound similar thereto with similar affinity to the specific alveolar GM-CSF receptor in the subject's airways and/or lung parenchyma to transform resting alveolar macrophage into immunoactive dendritic cells thereby ensuring normal or enhanced function of the pulmonary host defense.

In one embodiment, the subject is a mammal. In one embodiment, the mammal is a human. In one embodiment, the human is a child younger than 15 years of age. In one embodiment, the human is an adult 15 years of age or older.

The methods and compositions of the present invention are particularly useful in treating and/or alleviating symptoms secondary to irradiation injuries and/or the negative pulmonary effect on the pulmonary host defense mechanism after irradiation injuries, such as, but not limited to, inhalation of radioactive particles and/or systemic exposure to gamma radiation, and/or systemic administration of cancer chemotherapies. Recombinant GM-CSF or compounds with similar affinity to the pulmonary GM-CSF receptor, administered in an inhalable formulation, counteract the reduced pulmonary host defense in a number of conditions including, but not limited to, irradiation, inadvertent accidental radiation exposure to the lung tissue after radiation injury via direct gamma radiation exposure, inhalation of radioactive material, and other conditions wherein the pulmonary host defense is reduced due to reduced local alveolar GM-CSF production.

In one embodiment, methods and compositions of the present invention upregulate the reduced pulmonary host defense subsequent to systemic administration of cancer-chemotherapeutic medicaments which freely pass from the systemic pool into the alveolo-capillary membrane and reduce the cellular expression capacity of endogenous GM-CSF in the alveolar space.

In another embodiment, inhaled GM-CSF or compounds with similar affinity to the pulmonary GM-CSF receptor administered in accordance with the present invention enhance the pulmonary host defense following accidental irradiation, e.g. in an atomic plant and/or in a laboratory environment.

In another embodiment, methods and compositions of the present invention are used to enhance the pulmonary host defense after a terroristic action using radioactive contamination and/or deliberate nuclear atomic bombing.

In another embodiment, methods and compositions of the present invention enhance the pulmonary host defense before, during or after therapeutic radiation therapy such as anti-radiation therapy against cancer.

In another embodiment, GM-CSF or a compound with similar affinity to the pulmonary GM-CSF receptor can be administered via pulmonary administration to a subject with primary lung cancer and/or secondary lung cancer or metastatic cancer to enhance the lung's host defense mechanism reduced by the cancer.

By "administration via pulmonary administration" as used herein it is meant to be inclusive of all forms of intratracheal, intrabronchial, intraalveolar and inhalation administration whereby GM-CSF or a compound with similar affinity to the pulmonary GM-CSF receptor is applied into the trachea, the bronchi, small airways i.e. bronchioli, or the alveoli, respectively, whether by the instillation of a solution of GM-CSF or a compound with similar affinity to the pulmonary GM-CSF receptor via bronchoalveolar lavage, by applying GM-CSF or a compound with similar affinity to the pulmonary GM-CSF receptor in a powder form, or by allowing GM-CSF or a compound with similar affinity to the pulmonary GM-CSF receptor to reach the relevant part of the airway by inhalation of GM-CSF or a compound with similar affinity to the pulmonary GM-CSF receptor as an aerosolized or nebulized solution or powder, with or without added stabilizers or other excipients.

Pharmaceutical compositions or formulations for use in the present invention include GM-CSF or a compound with similar affinity to the pulmonary GM-CSF receptor in combination with, preferably dissolved in, a pharmaceutically acceptable carrier, preferably an aqueous carrier or diluent, or carried to the lower airways as a pegylated preparation or as a liposomal or nanoparticle preparation administered as an aerosol via inhalation, or as a lavage fluid administered via a bronchoscope as a bronchoalveloar lavage or as a blind intratracheal wash or lavage. A variety of aqueous carriers may be used, including, but not limited to 0.9% saline, buffered saline, physiologically compatible buffers and the like. The compositions may be sterilized by conventional techniques well known to those skilled in the art. The resulting aqueous solutions may be packaged for use or filtered under aseptic conditions and freeze-dried, the freeze-dried preparation being dissolved in a sterile aqueous solution prior to administration.

Preferred are formulations for inhalation.

The compositions may contain pharmaceutically acceptable auxiliary substances or adjuvants, including, without limitation, pH adjusting and buffering agents and/or tonicity adjusting agents, such as, for example, sodium acetate, sodium lactate, sodium chloride, potassium chloride, calcium chloride, etc.

What is claimed is:

1. A method for treating or alleviating symptoms of injuries to lung tissue secondary to systemic administration of a chemotherapeutic agent in a subject undergoing anti-cancer therapy, said method comprising administering to the subject receiving systemic administration of a chemotherapeutic agent an effective amount of recombinant granulocyte macrophage colony stimulating factor (GM-CSF) via pulmonary airway administration before, during and/or after systemic administration of the chemotherapeutic agent to the subject so that a pulmonary host defense mechanism in the subject is enhanced and symptoms of injuries to lung tissue secondary to systemic administration of the chemotherapeutic agent in the subject comprising reduced cellular expression capacity of endogenous granulocyte-macrophage colony-stimulating factor in the alveolar space are alleviated or treated.

2. The method of claim 1 wherein recombinant GM-CSF is administered via inhalation.

3. A method for alleviating negative pulmonary effects of systemic administration of a chemotherapeutic agent on a pulmonary host defense mechanism of a subject undergoing anti-cancer therapy, said method comprising administering to the subject receiving systemic administration of a chemotherapeutic agent an effective amount of recombinant granulocyte macrophage colony stimulating factor (GM-CSF) via pulmonary airway administration before, during and/or after systemic administration of the chemotherapeutic agent so that a pulmonary host defense mechanism in the subject is enhanced and negative pulmonary effects of systemic administration of the chemotherapeutic agent on a pulmonary host defense mechanism comprising reduced cellular expression capacity of endogenous granulocyte-macrophage colony stimulating factor in the alveolar space are alleviated.

4. The method of claim 3 wherein recombinant GM-CSF is administered via inhalation.

* * * * *